(12) United States Patent
Arrigo et al.

(10) Patent No.: US 7,914,481 B1
(45) Date of Patent: Mar. 29, 2011

(54) EPIDURAL NEEDLE FOR ELECTRODE EPIDURAL CATHETER AND METHOD OF MANUFACTURE

(75) Inventors: Anthony C. Arrigo, North Andover, MA (US); Raymond T. Charbonneau, Swansea, MA (US)

(73) Assignee: Spectra Medical Devices, Inc., Wilmington, MA (US)

( * ) Notice: Subject to any disclaimer, the term of this patent is extended or adjusted under 35 U.S.C. 154(b) by 490 days.

(21) Appl. No.: 11/897,646

(22) Filed: Aug. 30, 2007

(51) Int. Cl.
*A61M 31/00* (2006.01)
*A61M 37/00* (2006.01)
*A61M 5/178* (2006.01)

(52) U.S. Cl. .................. 604/60; 604/96.01; 604/164.12; 604/164.01

(58) Field of Classification Search ............... 604/96.01, 604/260, 164.01
See application file for complete search history.

(56) References Cited

U.S. PATENT DOCUMENTS

| | | | |
|---|---|---|---|
| 6,589,212 B1 * | 7/2003 | Navis | 604/164.01 |
| 2004/0122373 A1 * | 6/2004 | Botich et al. | 604/164.12 |
| 2006/0178646 A1 * | 8/2006 | Harris et al. | 604/268 |
| 2007/0265582 A1 * | 11/2007 | Kaplan et al. | 604/260 |
| 2008/0039894 A1 * | 2/2008 | Catanese et al. | 606/232 |
| 2009/0171276 A1 * | 7/2009 | Bednarek et al. | 604/96.01 |

* cited by examiner

*Primary Examiner* — Nicholas D Lucchesi
*Assistant Examiner* — Ian K Holloway
(74) *Attorney, Agent, or Firm* — Foley & Lardner LLP

(57) ABSTRACT

An epidural needle for placement of a pain management electrode includes an elongated bevel having a heel segment defined by a proximal rounded inner edge in which the heel has an electropolished radius of at least about 0.002 inch extending substantially continuously along the inner edge that defines the heel; a method for fabricating the needle.

9 Claims, 3 Drawing Sheets

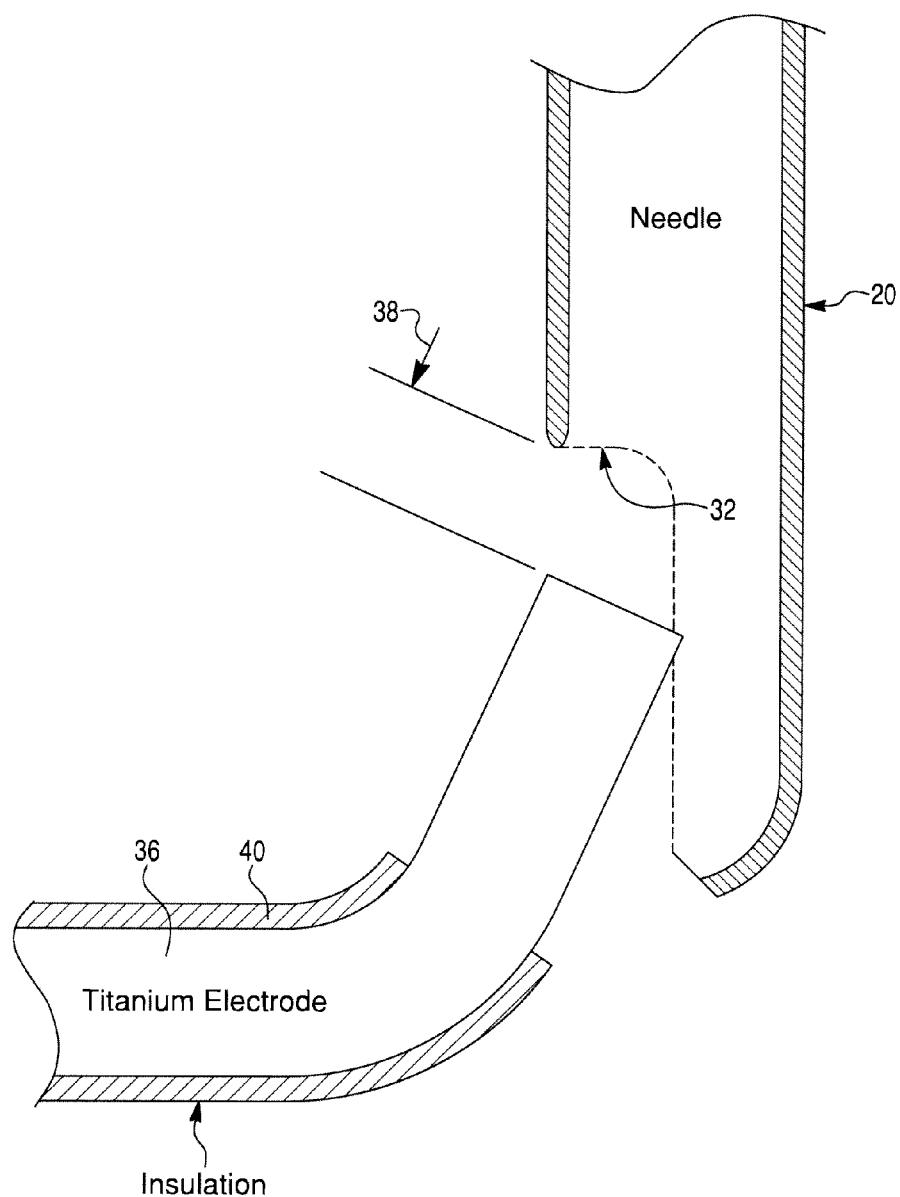

EPIDURAL NEEDLE FOR ELECTRODE EPIDURAL CATHETER AND METHOD OF MANUFACTURE

FIELD OF THE INVENTION

Epidural needles for placing electrode catheters for spinal cord stimulation.

BACKGROUND

Spinal cord stimulation (SCS) with electrical pulses is an accepted technique to treat certain patients having symptoms or conditions such as chronic pain, Parkinson's Disease, incontinence and epilepsy, among others. The treatment involves delivery of electrical pulses at selected locations along the spinal cord by electrode leads that are implanted within and extend along the epidural space of the spine. When such treatment is beneficial, the patient will experience a sensation (paresthesia) as the discomfort or other symptom is relieved. Such leads may be temporarily or permanently implanted. An important part of the procedure is the placement of the lead to locate the electrodes at its distal end at precisely the right location to affect the desired nerves. That involves adjustment in the position of the lead and monitoring feedback from the patient to determine the best position for the lead. When the best position is determined the lead is fixed in place. Lead placement also may be conducted under fluoroscopic visualization.

Leads may be placed surgically or in a less invasive, percutaneous, procedure. The percutaneous procedure involves insertion of a hollow needle into the epidural space so that the lead can be advanced through the lumen of the needle and then longitudinally along the dura of the spinal cord to the intended region of the spinal column. Typically, the position of the lead must be adjusted by advancing or retracting the lead through the needle and testing the effect of applying electrical pulses at various locations and with varying signals.

The leads typically are constructed to include a flexible elongate polymeric shaft with a plurality of electrodes mounted, at spaced locations, on the shaft. The electrodes are connected to wires that extend through the catheter to the proximal end of the catheter where they may be connected to a pulse generator. Some leads also may be placed with the aid of a stylet that is disposed within a lumen of the lead and can be manipulated by the physician Among the difficulties with placement of epidural SCS leads is that the transitions along the outer surface of the lead from polymer to electrode to polymer, etc. may have some irregularities that sometimes results in the transition regions of the catheter becoming caught or snagged on an edge of the needle, possibly damaging the catheter. This is particularly troublesome as the physician is attempting to adjust the position of the lead by advancing or retracting the lead through the needle. Although the needle may be provided with an elongate bevel at its distal end to enable the lead to bend at a relatively large radius to reduce snagging, it would be desirable, however, to provide additional means by which the advancement or retraction of the lead through the needle is made smooth and with still further reduced risk of catching. It is among the objects of at least the invention to provide improvements to that end.

SUMMARY OF THE INVENTION

The needle is provided with a selectively electropolished edge in the heel portion of the bevel. The polished edge is the proximal arcuate inner edge of the needle lumen where it transitions into the bevel. The inner edge is electropolished to form a radius over which the transitional regions of the catheter can pass without snagging or catching. In the preferred embodiment, the radius is of the order of about 0.002 inch and is substantially uniform along the arc defined by the edge.

DESCRIPTION OF THE DRAWINGS

In the accompanying drawings:
FIG. 3 is a somewhat diagrammatic illustration of the arrangement for electropolishing portions of the needle.

DESCRIPTION OF THE PREFERRED EMBODIMENT

Figure 1:
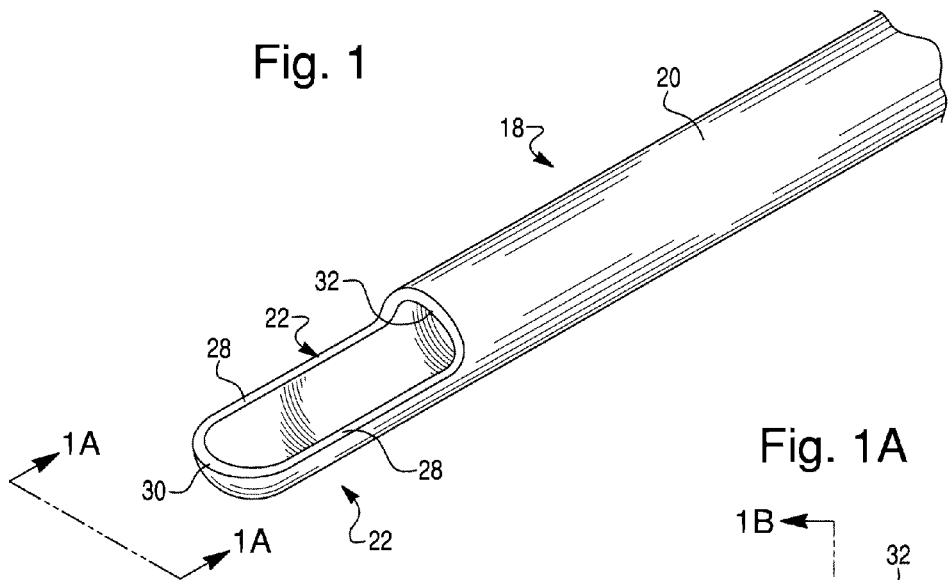
FIG. 1 is an isometric illustration of the distal end of a needle having an elongate bevel.
Figure 1A:
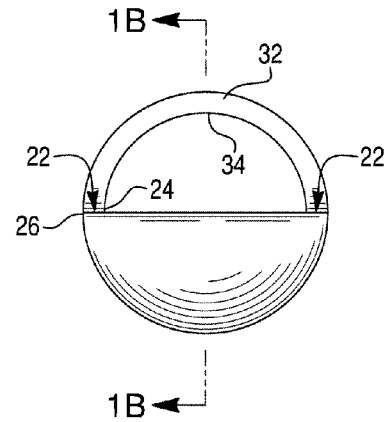
FIGS. 1A-1C are illustrations of the needle as seen along the planes 1A-1A, 1B-1B and 1C-1C of FIG. 1.
Figure 1C:
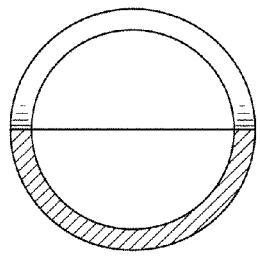
Figure 1B:
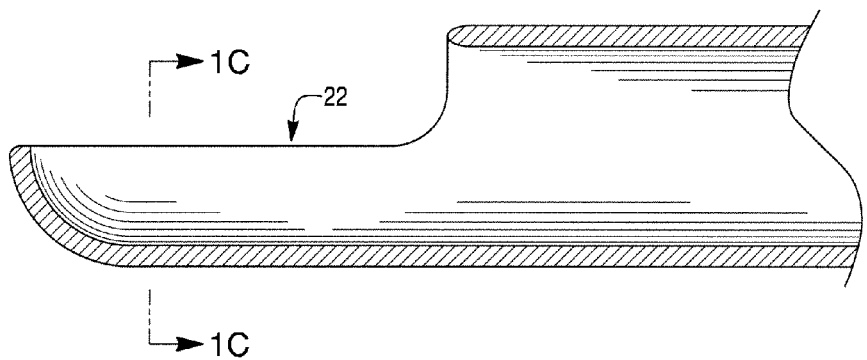
Figure 2:
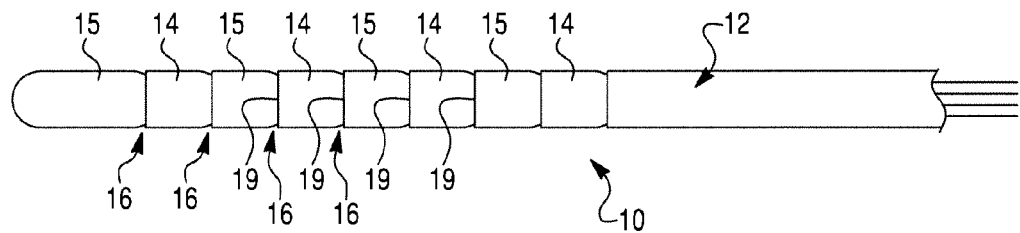
FIG. 2 is a somewhat diagrammatic illustration of a neurostimulation lead adapted to be placed through the needle into the epidural space and adjustably positioned along the spinal column.

FIG. 2 illustrates one type of catheter-like neurostimulation lead 10 adapted for placement within the epidural space. The lead 10 includes a flexible biocompatible polymeric body 12 and a plurality of electrodes 14 spaced longitudinally along the body. In the embodiment shown, the electrodes 14 and exposed segments 15 of the polymeric body 12 disposed between the electrodes may define an outer surface for the lead 10 having alternating bands of polymer and electrodes. The electrodes 14, which may be platinum or other suitable biocompatible metal, are connected by wires extending internally within the polymeric body 12 to connectors at the proximal end of the lead where they may be connected to a signal generator (not shown) that may be implanted within or located externally of the patient.

Figure 2A:
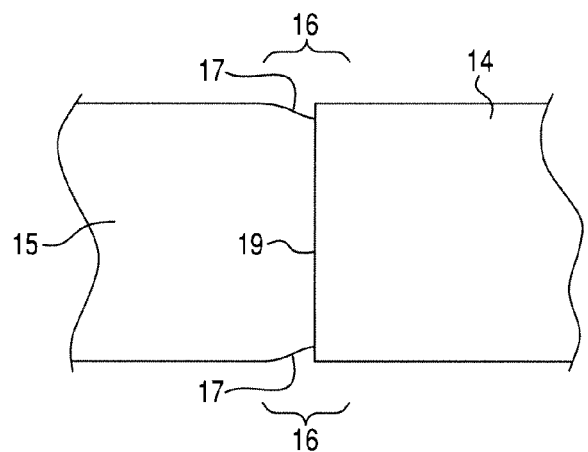
FIG. 2A is an enlarged illustration of a transitional region between a crimped ring electrode and the polymeric body of the lead.

FIG. 2A illustrates, in enlarged diagrammatic section, a portion of the lead 10 that includes the transition region 16 between an electrode 14 and an adjacent exposed portion 15 of the polymeric body 12. It is not uncommon for such leads to have at least some transitional regions 16 that do not present an even surface. In some cases, this may be the result of deliberate design or, in others, due to manufacturing tolerances. For example, when the electrode bands are crimped onto the lead body, the body in the transition region may be compressed, leaving a slight depression 17. The interruptions in the transitional regions 16 present a risk of a transitional region (e.g., at the edge 19 of an electrode 14) becoming caught on an edge of the introduction needle as the lead is withdrawn through the lumen of the needle, either during adjustment or placement of the lead. It would be desirable to provide a simple, inexpensive way to avoid this difficulty.

We have found that the risk of snagging of a neurostimulation lead during placement may be reduced significantly, and possibly eliminated, by electropolishing selected portions of the needle. As shown in FIGS. 1 and 1A-1C, the needle 18 is formed from stainless steel hypodermic tubing 20, for example, 14 gage to 22 gage. The tip 22 is elongated, having a long bevel 22 that may be of the order of about 0.2 to about 0.3 inch long with inner and outer edges 24, 26. The inner edge 24 of the bevel may be considered as having a pair of parallel, longitudinally extending sides 28, a tip segment 30 and a semicircular heel segment 32. The lumen-defining edge 34 of the heel segment 32 that results from the grinding of the bevel is susceptible to having burrs, irregular edges and the like that may become caught on a transitional region 16 of the lead 10 as the lead is manipulated through the needle. Typically, the manufacture of such needles involves abrasive blasting or wire EDM treatment of the tip to attempt to eliminate burrs or other irregularities resulting from the grinding of the tip. Other approaches involve the use of an abrasive cord that is threaded through the lumen of the needle and worked back and forth. These are relatively inefficient hand operations that may result in non-uniform surfaces and edges.

In accordance with the present invention, the heel region of the epidural needle is electropolished in a controlled manner, with the electropolishing process being focused on the heel of the bevel such that the inner edge 34 of the heel segment 32 is formed with a regular and uniform cross-sectional radius large enough to avoid catching on irregular transitional regions 16 of the neurostimulation lead 10. We have found that electropolishing the edge 34 to a radius of at least about 0.002 inch is sufficient to materially reduce the risk of, and possibly avoid, adverse interference between the heel 32 and the outer surfaces of the lead.

FIG. 3 illustrates in diagrammatic side view the manner in which the selective electropolishing may be conducted. The needle 20 is held in a fixture, as is a wire-like electropolishing electrode 36. The fixture supports the electrode (cathode) and needle in a relative orientation that will concentrate the energy applied between the electrode and the needle so that it is at its greatest intensity at the region of the heel segment 32. The electrode preferably is configured and positioned to provide substantially uniform energy density along the inner edge of the heel 32 to obtain a substantially consistent electropolished radius along the arcuate edge 34. The electrode should have a diameter no greater and, preferably, smaller than the inner diameter of the needle lumen to facilitate placement in close proximity to the heel. In a preferred embodiment, the tip of the electrode is directed toward the heel and preferably is held at a distance 38 between about 2 to about 3 millimeters from the heel 32. The electrode should be contained within an insulative jacket 40 heat shrunk onto the electrode with approximately 0.1 inch of the electrode protruding distally beyond the end of the jacket. The wire cathode 36 may be formed from titanium or copper and, for example, for a fifteen gauge needle, a cathode of the order of about 0.047 inch diameter may be employed. The needle and the electrode are immersed within any suitable electropolishing fluid for use with the metal from which the hypotube is made, for example, 300 series stainless steel. The duration, voltages, electric current and the temperature and specific gravity of the electropolishing fluid may be varied and selected. We have found that these parameters can be varied such that the operation can be completed in approximately two and one-half minutes and results in a very smooth, regular radius extending along the length of the arcuate edge of the heel. A plurality of such fixtures may be provided to conduct the electropolishing of needles in batch quantities with substantially greater efficiency and uniformity of results than with the prior hand abrading techniques.

It should be understood that the foregoing description of the invention is intended merely to be illustrative and that variations may be employed within the scope of the claims and their equivalents.

We claim:

1. An epidural needle for placement of a spinal stimulation lead in the epidural space comprising:
   a hypotube having a distal tip with an elongated bevel, a distal tissue piercing tip segment, and defining an inner edge and an outer edge at a juncture of the bevel with inner and outer diametral surfaces of the hypotube, respectively;
   the bevel having a heel segment in which the inner edge of the hypotube is rounded; and
   the rounded inner edge of the heel segment having a radius of at least about 0.002 inch extending substantially continuously along the heel segment.

2. A combination of the epidural needle of claim 1 and a spinal stimulation lead adapted to extend through the epidural needle,
   wherein the spinal stimulation lead has an outer surface with alternating bands of polymeric material and electrode material, and
   wherein the radius of the rounded inner edge of the heel segment is sufficient to prevent transition regions at the juncture of the polymeric material and electrode material from becoming caught on the rounded inner edge of the heel segment.

3. A method of forming a needle comprising:
   providing a hypotube;
   removing material at the distal tip to form an elongated bevel that includes a heel; and
   performing an electropolishing operation concentrated at the heel region to electropolish the heel inner edge to provide a smooth radius of at least about 0.002 inch.

4. The epidural needle of claim 1, wherein the inner edge is rounded by electropolishing.

5. An epidural needle for placement of a catheter in a body, comprising:
   a hypotube having a distal tip that includes:
      an elongated bevel;
      a distal tissue piercing tip segment; and
      at least an inner edge at a juncture of the bevel with an inner diametral surface of the hypotube,
   wherein the bevel has a heel segment in which the inner edge is rounded, wherein the inner edge is rounded substantially continuously along the heel segment and in an amount sufficient to prevent snagging of a catheter on the inner edge as the catheter is moved during placement, and
   wherein the rounded inner edge of the heel segment has a radius of at least about 0.002 inch.

6. The epidural needle of claim 5, wherein the inner edge of the heel segment is rounded by electropolishing.

7. A combination comprising:
   an epidural needle including a hypotube having a distal tip that includes:
      an elongated bevel;
      a distal tissue piercing tip segment; and
      at least an inner edge at a juncture of the bevel with an inner diametral surface of the hypotube; and
   a catheter adapted to move through the epidural needle for placement,
   wherein the bevel of the epidural needle has a heel segment in which the inner edge is rounded, wherein the inner edge is rounded substantially continuously along the heel segment and in an amount sufficient to prevent snagging of a catheter on the inner edge as the catheter is moved during placement, and
   wherein the rounded inner edge of the heel segment has a radius of at least about 0.002 inch.

8. The combination of claim 7, wherein the inner edge of the heel segment is rounded by electropolishing.

9. The combination of claim 7,
   wherein the catheter has an outer surface with alternating bands of polymeric material and electrode material, and
   wherein the radius of the rounded inner edge of the heel segment is sufficient to prevent transition regions at the juncture of the polymeric material and electrode material from becoming caught on the inner edge of the heel segment.

* * * * *